United States Patent [19]

Kirschner et al.

[11] Patent Number: 6,015,715
[45] Date of Patent: Jan. 18, 2000

[54] METHOD OF MANUFACTURING A SENSITIVE SINGLE-LAYER SYSTEM FOR MEASURING THE CONCENTRATION OF ANALYTES, AND A SYSTEM PRODUCED BY THIS METHOD

[76] Inventors: Uwe Kirschner, Alttrachau 41, Dresden 01139, Germany; Matthias Lau, Blasewitzer Strasse 22, Dresden 01307, Germany; Birgit Hannemann, Augsburger Strasse 44, Chemnitz 09126, Germany; Adriana Tamachkiarowa, 17 Januari, Sliven 8800, Bulgaria

[21] Appl. No.: 08/952,506

[22] PCT Filed: May 24, 1996

[86] PCT No.: PCT/DE96/00915

§ 371 Date: Jan. 6, 1998

§ 102(e) Date: Jan. 6, 1998

[87] PCT Pub. No.: WO96/37768

PCT Pub. Date: Nov. 28, 1996

[30] Foreign Application Priority Data

May 27, 1995 [DE] Germany .................. 195 19 496

[51] Int. Cl.[7] .................. G01N 21/64; G01N 33/48
[52] U.S. Cl. .................. 436/166; 436/164; 436/172; 422/58; 422/82.08
[58] Field of Search .................. 422/82.05–82.08, 422/58; 356/402; 436/164, 166, 172

[56] References Cited

U.S. PATENT DOCUMENTS

| | | |
|---|---|---|
| 5,039,490 | 8/1991 | Marsoner et al. . |
| 5,408,999 | 4/1995 | Singh et al. . |

FOREIGN PATENT DOCUMENTS

| | | |
|---|---|---|
| 390678 | 6/1990 | Austria . |
| 0190829 | 8/1986 | European Pat. Off. . |
| 0190830 | 8/1986 | European Pat. Off. . |
| 0244394 | 11/1987 | European Pat. Off. . |
| 0313655 | 5/1989 | European Pat. Off. . |
| 0344313 | 12/1989 | European Pat. Off. . |
| 0354204 | 2/1990 | European Pat. Off. . |
| 0417535 | 3/1991 | European Pat. Off. . |
| 0578630 | 1/1994 | European Pat. Off. . |
| 2823318 | 11/1979 | Germany . |
| 3148830 | 6/1983 | Germany . |
| 3346810 | 7/1984 | Germany . |
| 3702210 | 7/1987 | Germany . |
| 4108808 | 9/1992 | Germany . |
| 1190583 | 5/1970 | United Kingdom . |
| 8800339 | 1/1988 | WIPO . |
| 9410553 | 5/1994 | WIPO . |

OTHER PUBLICATIONS

Egli et al., Gasttrennung mittels Membranen, Swiss. Chem., 6, 1984, pp. 89–126.

Lippitsch et al., "Fibre–Optic Oxygen Sensor with the Flourescence Decay Time as the Information Carrier", Analytica Chemica Acta 205, 1988, pp. 1–6.

Wenying Xu et al., "Oxygen Sensors Based on Luminescence Quenching: Interactions of Metal Complexes with the Polymer Supports", Anal. Chem., 66, 1994, pp. 4133–4141.

Bacon et al., "Determination of Oxygen Concentrations by Luminescence Quenching of a Polymer–Immobilized Transition–Metal Complex", Anal. Chem., 59, 1987, pp. 2780–2785.

*Primary Examiner*—Lyle A. Alexander
*Attorney, Agent, or Firm*—Greenblum & Bernstein, P.L.C.

[57] ABSTRACT

Method of manufacturing a sensitive single-layer system for optically detecting a concentration of an analyte, such as, for example, oxygen, the analyte being capable of investigation in liquid or gaseous aggregate condition or in a dissolved condition, by adsorption, luminescence or luminescence quenching of an indicator sensitive to the analyte, which is preferably permanently immobilized in the optical beam path. The sensitive single-layer system achieves a reproducible and extremely short response behavior. Indicators are adsorbed on a filler material and thereafter a mixture is produced with a matrix material permeable to the analyte to be detected. Then, under the action of pressure, the mixture is extruded onto a substrate, the layer thickness being formed in dependence on the applied pressure used. The applied sensitive layer is polymerized, polycondensed or hardened and the layer is also homogenized by swelling in a fluorescence indicator solution.

31 Claims, 1 Drawing Sheet

METHOD OF MANUFACTURING A SENSITIVE SINGLE-LAYER SYSTEM FOR MEASURING THE CONCENTRATION OF ANALYTES, AND A SYSTEM PRODUCED BY THIS METHOD

BACKGROUND OF THE INVENTION

1. Field of the Invention

The invention relates to a method of producing a sensitive single-layer system for optical detection of the concentration of an analyte, such as, for example, oxygen. The analyte is capable of being investigated in the liquid or gaseous aggregate condition, or in a dissolved form, by absorption, luminescence or luminescence quenching of an indicator sensitive to the analyte. The indicator is preferably permanently immobilized in the optical beam path.

The invention further relates to a single-layer sensitive system including single-layer sensitive systems produced according to this method.

2. Discussion of Background Information

Systems and methods for determining the $O_2$ partial pressure or $O_2$ concentration by dynamic luminescence quenching of ruthenium-α-diimine complexes using optical waveguides have been described in EP 0 190 829, EP 190 830, EP 0 313 655, EP 0 344 313, DE 33 46 810, DE 37 02 210 and DE 41 08 808.

In this case $[Ru(biPY)_3]^{2+}$, $[Ru(phen)_3]^{2+}$, or $[Ru(4,7Ph_2phen)_3]^{2+}$ are used as a counter-ion in combination with chloride or perchlorate as a ruthenium complex whose phosphorescence is quenchable by oxygen. These indicator pigments are immobilized in polysiloxane matrix materials permeable to oxygen and therein are applied to glass fibers. Polysiloxanes with differing substituents and additives as well as specific layer sequences or protective membranes are proposed. Further, an arrangement of the indicator matrix system on the glass fibers is named, which can be ground at a specific angle.

In EP 190 829 a plurality of plasticisers are proposed as additives to the matrix material, which in this case is disposed on a fiber ground at an angle of 20° to 30°. As described in EP 190 830, the indicator matrix system can partly represent also the optical periphery of the fiber. In EP 0 313 655=WO 88/00339, without fastening on a specific material, an optically transparent matrix material is proposed, upon which the indicator is adsorbed or in which it is immobilized.

In EP 0 344 313 there is proposed a layer sequence of transparent substrate, indicator and gas-permeable membrane. According to DE 33 46 810, in addition to a plurality of indicators, among which are also found ruthenium compounds, and matrix polymers, among which are also polysiloxanes, special forms of the matrix, such as lamellae, spheres and films, but also solid additives such as silica gel, are proposed. In addition, various methods of introducing the indicator into the matrix are described, such as inward diffusion, mechanical mixing or covalent binding; additional protective layers are also named. The document DE-PS 37 02 210 describes the use of a two-component silicon polymer.

Finally, DE 41 08 808 proposes an indicator-containing silicon membrane convexly spread on a transparent substrate.

There is further described in DE 31 48 830 a device for determining the oxygen concentration in gases, liquids and tissues, in which a single-size layer is present on a transparent carrier with a luminescent surface formed with an adhesive or glue layer, an evaluable signal being intended to be obtained by irradiation with light at a specific wave length. The single-sized layer in this case is formed from a luminescent pigment itself or an inert carrier adsorbing this pigment, such as silica gel, or another water-rejecting plastic.

In GB 1 190 583 a gas sensor is disclosed, in which a luminescent material is taken up into a permeable or porous carrier matrix material, the matrix material preferably being a natural or synthetic polymer or porous glass.

There may be seen from EP 0 417 535 an optical oxygen sensor, in which oxygen indicator molecules are incorporated in a polymer. As an example of such a polymer, polydimethylsiloxane is disclosed, which is intended to be used as a carrier for the oxygen indicators. The polymers used are then dissolved in a solvent which contains the oxygen indicators. The solution is then applied in a thin layer to the substrate and hardened; only an indirect influence can be exerted on the layer thickness formed, and thus reproducible results are not always achievable.

In the sensor member described in EP 0 244 394 for determining material concentrations in gaseous and liquid samples, a carrier layer and an indicator layer with at least one indicator substance are named. In this case at least one photosensitive member is applied to the carrier layer.

A fiber-optic system for determining parameters in fluids is described in WO 94/10553. Here a fluorescent pigment is adsorbed from a solution onto a solid carrier, and, mixed with a liquid silicone, applied to a carrier; in this case for example polydimethylphenylsiloxane or unhardened polydimethylsiloxane may be used as a silicone in addition to others. The indicator matrix further contains indicator molecules on a carrier. A permeable membrane protects the indicator matrix, and the carrier in addition contains porous glass particles or a porous material based on silica gel or other porous glass particles and a carrier polymer of a non-ionic gel. Ru(1,10-phenanthroline) chloride is proposed as a possible indicator.

In the sensor member described in AT 390 678 for determining material concentrations, the use of an indicator layer consisting of polymer with a fluorescence indicator is proposed. The indicator layer is intended to consist of a porous glass layer, in which the indicator substance is immobilized. The indicator layer in this case can be a porous glass layer or a spun-on or rolled-on silicone layer, in which the indicator substance is present.

A similar device is also described in EP 0 578 630, in which case the sensor membrane of an optical sensor for determining a physical or chemical parameter of a sample is likewise intended to have a polymer matrix with an immobilized indicator substance.

In the optical sensor described in EP 0 354 204, carrier particles of silica gel spheres are proposed, which are irreversibly bound to a fluorescence indicator.

The possible use of an adsorbent such as silica gel upon which a heterocyclic organic fluorescent dye stuff is adsorbed, can be seen in DE 28 23 318.

In Lippitsch, Max E. Et al.: "Fiber-Optic Oxygen Sensor with the Fluorescence Decay Time as the Information Carrier," in: Analytica Chimica Acta, 205, 1988, pp. 1 to 6, M. Lippitsch describes a fiber-optic oxygen sensor.

Exploitation of the alteration in luminescence for an oxygen sensor is likewise to be seen in an article by Wenying; Xu, et. al., "Oxygen Sensors Based on Luminescence Quenching: Interactions of Metal Complexes with the Polymer Supports," in: "Anal. Chem. 1994", 66, pp. 4133–4141. Here it is proposed to use the oxygen influence on [Ru(Ph$_2$phen)$_3$]Cl$_2$(Ph$_2$phen=4,7-diphenyl-1,10-phenanthroline) in combination with a polymer, such as, for example, polydimethylsiloxane. In addition silica gel is to be added, in order to be able to influence the sensor properties.

Ruthenium compounds are generally advantageous and appropriate for the named case of application due to their large Stokes Shift (large distance between energization and emission) and the relatively long-wave energization and emission; in this connection these are already widely described in the literature (see among others J. R. Bacon, K. N. Demas, "Determination of Oxygen Concentrations by Luminescence Quenching of a Polymer-Immobilised Transition-Metal Complex," Anal. Chem. 59, 2780–85, 1987).

Polysiloxanes are the polymers which have the greatest permeability for oxygen (see among others S. Egli, A. Ruf, A. Buck; Gastrennung mittels Membranen; Swiss. Chem. 6, 39–126, 1984).

Initially, a sufficient strength of the indicator-matrix systems is of great importance for practical use of such sensors. This is not sufficiently provided in the bonding of the indicator merely to the surface of a carrier. Furthermore, short response times, reproducible in the case of various examples of applicators, are to be achievable. The response times increase significantly, even in the case of polymers with good oxygen permeability, as the layer thickness increases or additional protective layers are applied.

It is therefore the object of the present invention to provide a method of manufacturing a sensitive single-layer system, and a sensitive single-layer system for measuring the concentration or the partial pressure of analytes, by means of which a reproducible and extremely short response behavior becomes obtainable.

According to the invention, the sensitive single-layer system is produced in such a way that the fluorescence indicators are adsorbed on to a filling material, and in connection therewith a mixture is produced with a matrix material permeable to the analyte to be investigated. The mixture produced is then compressed under the action of pressure, advantageously at an applied pressure of 12 to $20 \times 10^4$ Pa, preferably $15 \times 10^4$ Pa on a substrate, the layer thickness being formed in dependence on the applied pressure used. The sensitive layer thus applied is polymerized, polycondensed or hardened, this preferably being carried out in an extrusion mould to be used. The layer is additionally homogenized by swelling in a fluorescence indicator solution.

In order to swell the permeable matrix material, which is preferably polydimethylsiloxane, a methylene chloride solution containing a fluorescence indicator with a concentration of $10^{-1}$ to $10^{-6}$, preferably $10^{-3}$ to $10^{-4}$ molar concentration is used. The sensitive single layer system thus produced has in the sensitive layer an overall concentration of the fluorescence indicators in the permeable matrix of $10^{-1}$ to $10^{-6}$ mol/l, preferably $10^{-2}$ to $10^{-3}$ mol/l. Furthermore, a filler is also contained in the matrix with a weight proportion of 5 to 65% by weight, preferably 20 to 30% by weight. In this respect in an advantageous way silica gel porous glass should be used as a filler, upon which the fluorescence indicators are adsorbed.

Ruthenium-diamine complexes are advantageously used as fluorescence indicators, these more preferably being Ru(4,7ph$_2$phen)$_3$Cl$_2 \times 5$H$_2$O and being particularly suitable for detecting oxygen concentration.

An oxygen-permeable matrix material is for example polysiloxane and preferably polydimethylsiloxane.

The substrate material can be an optically transparent or reflective material and can be used in various forms. The sensitive layer can be applied to the substrate in accordance with the measuring purpose envisaged.

The sensitive single-layer system manufactured and designed according to the invention can be used for process monitoring in the most varied areas of technology and medicine, in order to monitor the concentration of analyte, particularly of oxygen, in almost any fluids, materials, mixtures of materials, and if necessary to utilize the measurement signals for influencing specific processes. Thus, in particularly the response time in millisecond range of the system according to the invention, in comparison to solutions previously known, is a positive factor. This is achieved by the capacity to produce extremely thin layers under pressure action with good adhesion and resistance. However, the most varied analyses may be carried out and supported, one example being the investigation of soil samples.

The sensitive single-layer system according to the invention can operate without additional adhesion promoters and protective layers. This is advantageously achieved by true-to-form polymerization, polycondensation or hardening and subsequent homogenization of the indicator matrix system on the substrate. An optical fiber or an optically transparent or reflective substrate can in this case preferably serve as a substrate.

A fiber optic applicator which may be manufactured according to the invention for a sensor system for optical detection of the concentration or of the partial pressure of an analyte, by adsorption, luminescence or luminescence quenching of an indicator immobilized in a permeable matrix material, is advantageously characterized in that good chronological durability and resistance in the utility medium even in flowing liquids, and further a signal level sufficient for good resolution, low response times, very low copy scatter of the values measured with various applications, and not least simplicity of manufacture, have been achieved.

The invention will be explained in more detail in the following with reference to an embodiment given by way of example.

Figure 1:
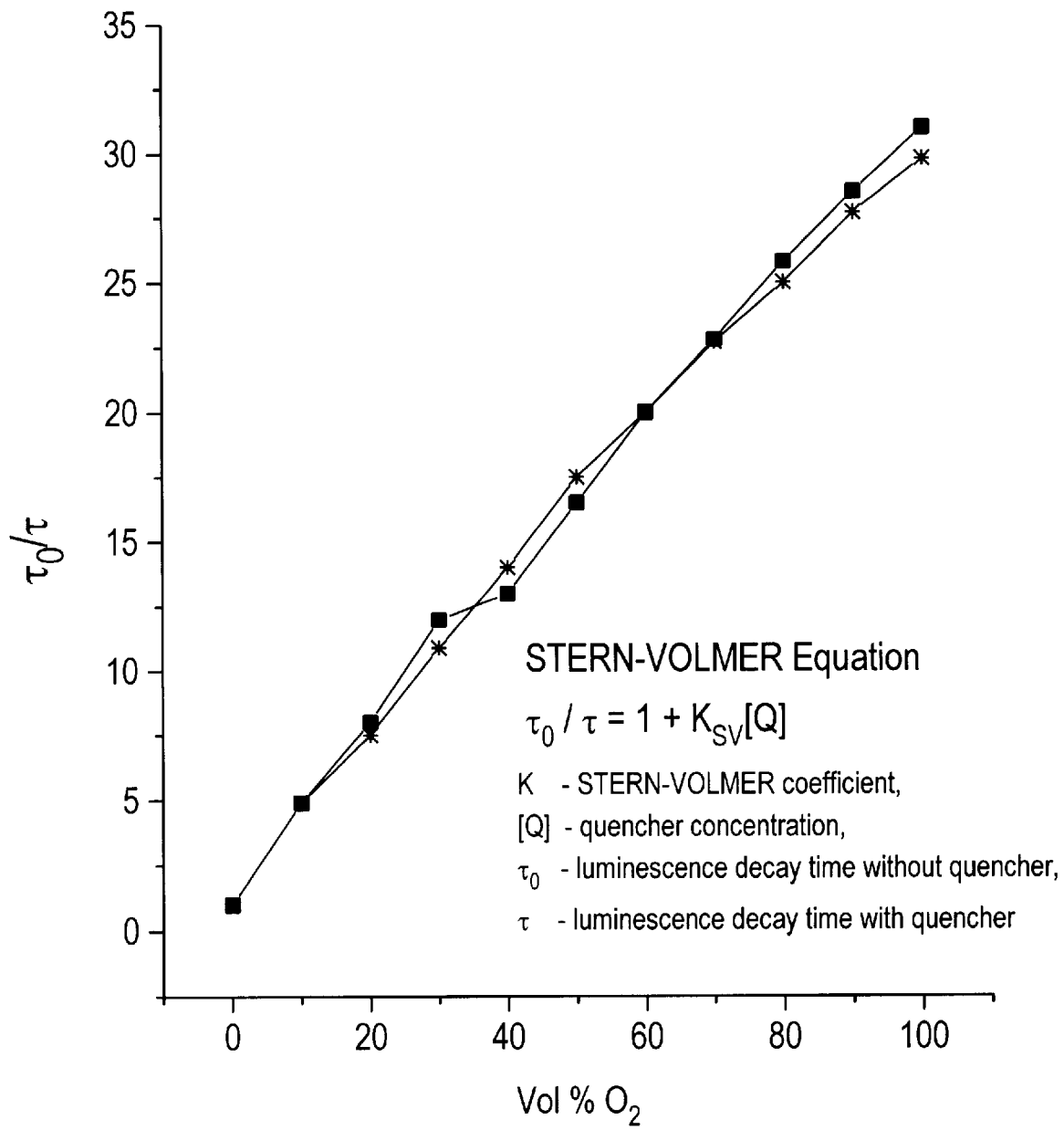
FIG. 1: a graphical view of the sensor characteristic curve of the single-layer system after manufacture and after 4 months' storage.

In order to produce the applicator, an appropriate filler material such as silica gel is treated with a solution of the indicator in a suitable solvent. After adsorption of the indicator on the filler material, excess solvent is removed. The desired quantity of filler material is mixed into a prepolymer or plasticised polymer, which is preferably permeable to the material to be detected after hardening, and the mass is pressed on to the substrate in a mould with a pressure which in conjunction with the geometry and size of the mould determines the layer thickness and the layer shape. The pressure action can however also be effected by other appropriate methods, e.g. by the use of profiled rollers or presses. Thus an indicator matrix may be produced with a defined thickness and shape on the substrate.

In this example, after the polymer is hardened, the indicator distribution is homogenized by swelling the layer located on the substrate in a solution of the same indicator, with final rinsing with solvent and drying.

The preferred embodiment described in the following relates to an applicator for an optical sensor system for detecting the oxygen concentration or the oxygen partial pressure by luminescence quenching of a ruthenium-α-diamine compound immobilized in polysiloxane.

A silica gel of suitable consistency is treated in a $10^{-4}$ molar solution $Ru(4,7ph_2phen)_3Cl_2 \cdot 5\ H_2O$ in methylene chloride until it is discolored.

After the silica gel is dried, corresponding proportions by weight of silica gel and corresponding proportions by weight of polydimethylsiloxane prepolymer are well mixed and painted in extrusion dyes. Thereafter the substrate is pressed into the dyes at a pressure of $15 \times 10^4$ Pa. The film thickness can be correspondingly adjusted via the pressure. The dye used should be so designed that the substrate may also be taken up and held in a defined way, so that the sensitive layer is formed in the desired shape, position and thickness.

After hardening the polydimethylsiloxane, the coverings are subjected in a subsequent swelling in an indicator-containing methylene chloride solution, and then are thoroughly rinsed and dried.

The resulting substrate is covered with a securely-adhering indicator matrix film which is also extremely stable in solutions, and which forms the actual sensitive layer.

Advantageously, the substrate should be optically transparent or reflective, in order to avoid losses.

An optical fiber or a fiber bundle may advantageously be used as a substrate. It may also however be in the form of an optically transparent plate or an optically transparent member or reflective member of the type of a lens, GRIN lens or of a prism. It may likewise be an integrated optical system, comprising a plurality of appropriate optical members.

As FIG. 1 shows, the sensor characteristic curve (Stern Volmer equation) of such a layer, deposited on a glass fiber with a core diameter of 400 μm, is shown on the one hand immediately after manufacture and on the other hand after a period of 4 months.

We claim:

1. Method of manufacturing a single-layer system for measuring concentration of analytes, comprising:
   adsorbing fluorescence indicator on filler material forming fluorescence indicator adsorbed filler material;
   mixing the fluorescence indicator adsorbed filler material with a permeable matrix material forming a mixture;
   applying the mixture under a pressure of 12 to $20 \times 10^4$ Pa onto a substrate to obtain a sensitive layer having a thickness and shape;
   polymerizing, polycondensing or hardening the matrix material; and
   homogenizing the layer by swelling with a solvent capable of dissolving the fluorescence indicator.

2. The method according to claim 1, wherein the applying comprises extruding the mixture into a mold to obtain the sensitive layer on a position on the substrate.

3. The method according to claim 1, wherein the permeable material comprises polydimethylsiloxane.

4. The method according to claim 1, wherein the solvent comprises methylene chloride.

5. The method according to claim 1, wherein the filler material comprises member selected from the group consisting of silica gel and porous glass.

6. The method according to claim 1, wherein the applying under pressure comprises compressing in a mold.

7. The method according to claim 1, wherein the matrix material comprises a polysiloxane.

8. The method according to claim 1, wherein the substrate comprises a reflective substrate.

9. The method according to claim 1, wherein the substrate comprises a reflective substrate.

10. The method according to claim 1, wherein the substrate comprises a member selected from the group consisting of an optical fiber, a bundle of optical fibers, a plate, a lens, a prism and an integrated optical structure.

11. Sensitive-single layer system produced by the method according to claim 1.

12. The method according to claim 1, wherein the applying under pressure comprises utilizing a pressure of $15 \times 10^4$ Pa.

13. Sensitive-single layer system produced by the method according to claim 12.

14. The method according to claim 1, wherein the permeable material comprises a polysiloxane; the solvent comprises a solution containing the fluorescence indicator in a molar concentration of $10^{-1}$ to $10^{-6}$; the layer includes an overall concentration of fluorescence indicator in the matrix of $10^{-1}$ to $10^{-6}$ mol/l; the filler material comprises a member selected from the group consisting of silica gel and porous glass; and the filler material is contained in the matrix material with a weight proportion of 5 to 65% by weight.

15. Sensitive-single layer system produced by the method according to claim 14.

16. The method according to claim 1, wherein the fluorescence indicator comprises a ruthenium-diamine complex.

17. Sensitive-single layer system produced by the method according to claim 16.

18. The method according to claim 1, wherein the solvent comprises a solution containing the fluorescence indicator in a molar concentration of $10^{-1}$ to $10^{-6}$.

19. The method according to claim 18, wherein the solvent comprises a solution containing the fluorescence indicator in a molar concentration of $10^{-3}$ to $10^{-4}$.

20. The method according to claim 18, wherein the solution comprises a methylene chloride solution.

21. Sensitive-single layer system produced by the method according to claim 18.

22. The method according to claim 1, wherein the layer includes an overall concentration of fluorescence indicator in the matrix of $10^{-1}$ to $10^{-6}$ mol/l.

23. The method according to claim 22, wherein the layer includes an overall concentration of fluorescence indicator in the matrix of $10^{-2}$ to $10^{-4}$ mol/l.

24. Sensitive-single layer system produced by the method according to claim 22.

25. The method according to claim 1, wherein the filler material is contained in the matrix material with a weight proportion of 5 to 65% by weight.

26. The method according to claim 25, wherein the filler material is contained in the matrix material with a weight proportion of 20 to 30% by weight.

27. The method according to claim 25, wherein said filler material comprises silica gel.

28. The method according to claim 25, wherein said filler material comprised porous glass.

29. Method of manufacturing a single-layer system for measuring concentration of analytes, comprising:
   adsorbing fluorescence indicator on filler material forming fluorescence indicator adsorbed filler material;
   mixing the fluorescence indicator adsorbed filler material with a permeable matrix material forming a mixture;
   applying the mixture under pressure onto a substrate to obtain a sensitive layer having a thickness and shape;

polymerizing, polycondensing or hardening the matrix material;

homogenizing the layer by swelling with a solvent capable of dissolving the fluorescence indicator; and wherein the substrate comprises a lens, and said lens comprises a GRIN lens.

30. Method of manufacturing a single-layer system for measuring concentration of analytes, comprising:

adsorbing indicator on filler material forming indicator adsorbed filler material;

mixing the indicator adsorbed filler material with a permeable matrix material forming a mixture;

applying the mixture under a pressure of 12 to $20 \times 10^4$ Pa onto a substrate to obtain a sensitive layer having a thickness and shape;

polymerizing, polycondensing or hardening the matrix material; and homogenizing the layer by swelling with a solvent capable of dissolving the indicator.

31. Sensitive-single layer system produced by the method according to claim 30.

* * * * *